United States Patent
Pazart et al.

(10) Patent No.: US 9,743,877 B2
(45) Date of Patent: Aug. 29, 2017

(54) DEVICE FOR TAKING A SAMPLE OF A BODY FLUID AND METHOD FOR IMPLEMENTING SAME

(75) Inventors: Lionel Pazart, Besançon (FR); Bruno François Marcel Wacogne, Traitiefontaine (FR); Christian Gérard Daniel Pieralli, Besançon (FR); Wilfrid Hervé Boireau, Mondon (FR); Pascal Charles Serge Morel, Besançon (FR)

(73) Assignees: Centre National de la Recherch Scientifique, Paris (FR); Centre Hospitalier Universitaire De Besancon, Besancon (FR); Universite De Franche Cornte, Beasancon (FR); Etablissement Francais Du Sang, La Plaine Saint Denis (FR)

( * ) Notice: Subject to any disclaimer, the term of this patent is extended or adjusted under 35 U.S.C. 154(b) by 1011 days.

(21) Appl. No.: 13/508,185

(22) PCT Filed: Oct. 29, 2010

(86) PCT No.: PCT/FR2010/000712
§ 371 (c)(1),
(2), (4) Date: Sep. 28, 2012

(87) PCT Pub. No.: WO2011/055029
PCT Pub. Date: May 12, 2011

(65) Prior Publication Data
US 2013/0030263 A1      Jan. 31, 2013

(30) Foreign Application Priority Data

Nov. 5, 2009   (FR) .................................... 09 05330

(51) Int. Cl.
*A61B 5/1455* (2006.01)
*A61B 5/157* (2006.01)
(Continued)

(52) U.S. Cl.
CPC .......... *A61B 5/157* (2013.01); *A61B 5/15003* (2013.01); *A61B 5/153* (2013.01);
(Continued)

(58) Field of Classification Search
CPC .................................................. A61B 5/1455
See application file for complete search history.

(56) References Cited

U.S. PATENT DOCUMENTS

| 4,014,328 A | 3/1977 | Cluff et al. |
| 4,865,583 A | 9/1989 | Tu |

(Continued)

FOREIGN PATENT DOCUMENTS

WO   WO 2006/088771 A2   8/2006

OTHER PUBLICATIONS

International Search Report and Written Opinion for Application No. PCT/FR2010/000712 dated Feb. 16, 2011.

*Primary Examiner* — Eric Winakur
*Assistant Examiner* — Marjan Fardanesh
(74) *Attorney, Agent, or Firm* — Alston & Bird LLP

(57) ABSTRACT

The invention relates to a device (200) for taking a sample of a body fluid, such as blood, to be incorporated into a fluid circuit of a perfusion (100) of a patient who has a perfusion catheter (104), said device having a tubular structure (202) for connecting to the fluid circuit of the perfusion, provided with a zone for intubation, during use, of a sampling channel (300) comprising a distal end (301); and a means (203) for holding, during use, in the tubular structure, the part of the sampling channel (300) comprising a distal end (301) in such a way that the distal end (301) is oriented towards the (Continued)

perfusion catheter (104), in the direction of flow (F1) of the perfusion product (102), from a perfusion product reservoir (101) towards the perfusion catheter (104).

6 Claims, 7 Drawing Sheets

(51) Int. Cl.
  *A61B 5/15* (2006.01)
  *A61B 5/153* (2006.01)
  *A61B 5/155* (2006.01)

(52) U.S. Cl.
  CPC ........ *A61B 5/155* (2013.01); *A61B 5/150221* (2013.01); *A61B 5/150992* (2013.01)

(56) References Cited

U.S. PATENT DOCUMENTS

| | | |
|---|---|---|
| 4,981,140 A | 1/1991 | Wyatt |
| 5,372,143 A | 12/1994 | Bernes et al. |
| 2008/0021381 A1 | 1/2008 | Lurvey et al. |

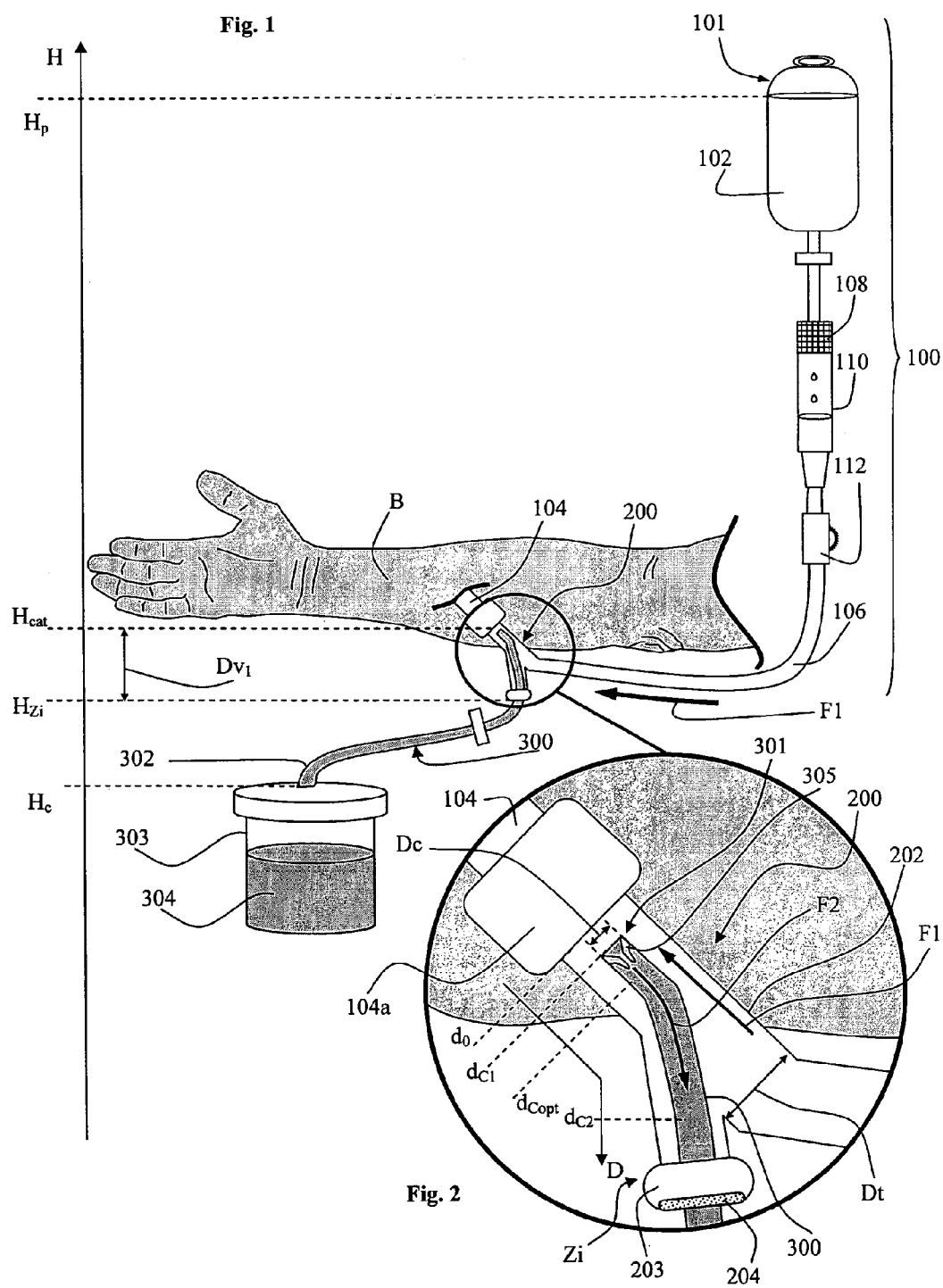

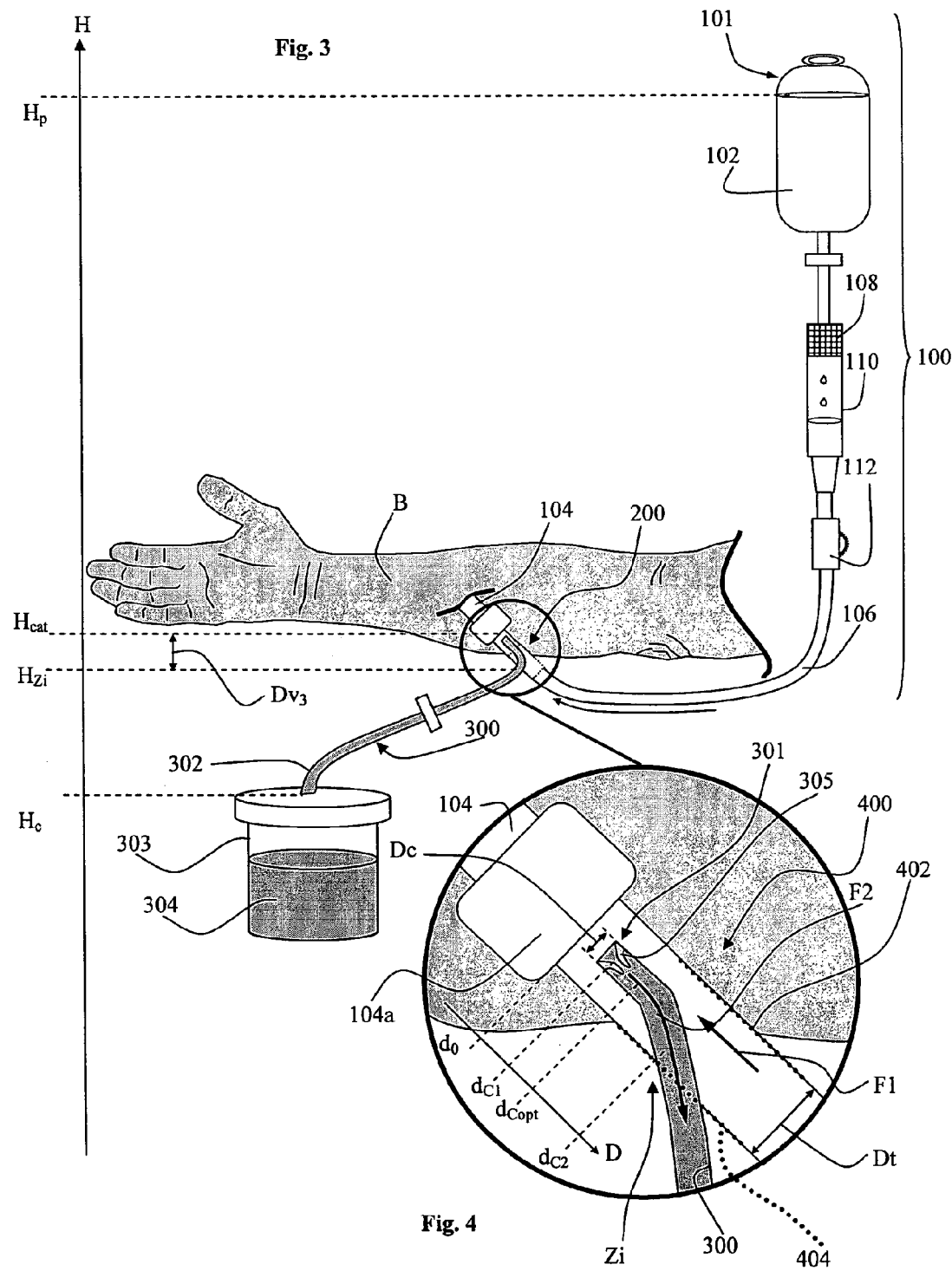

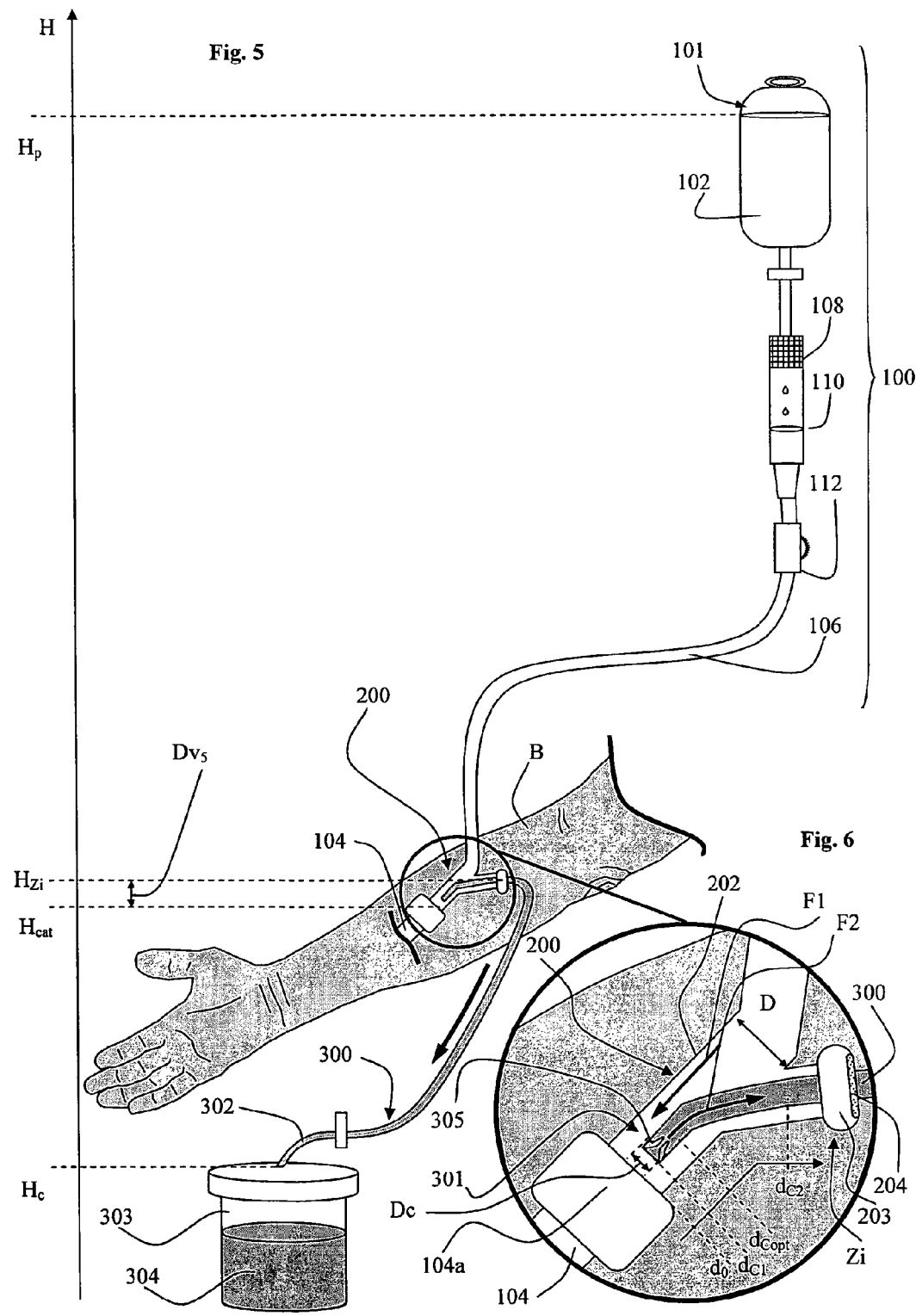

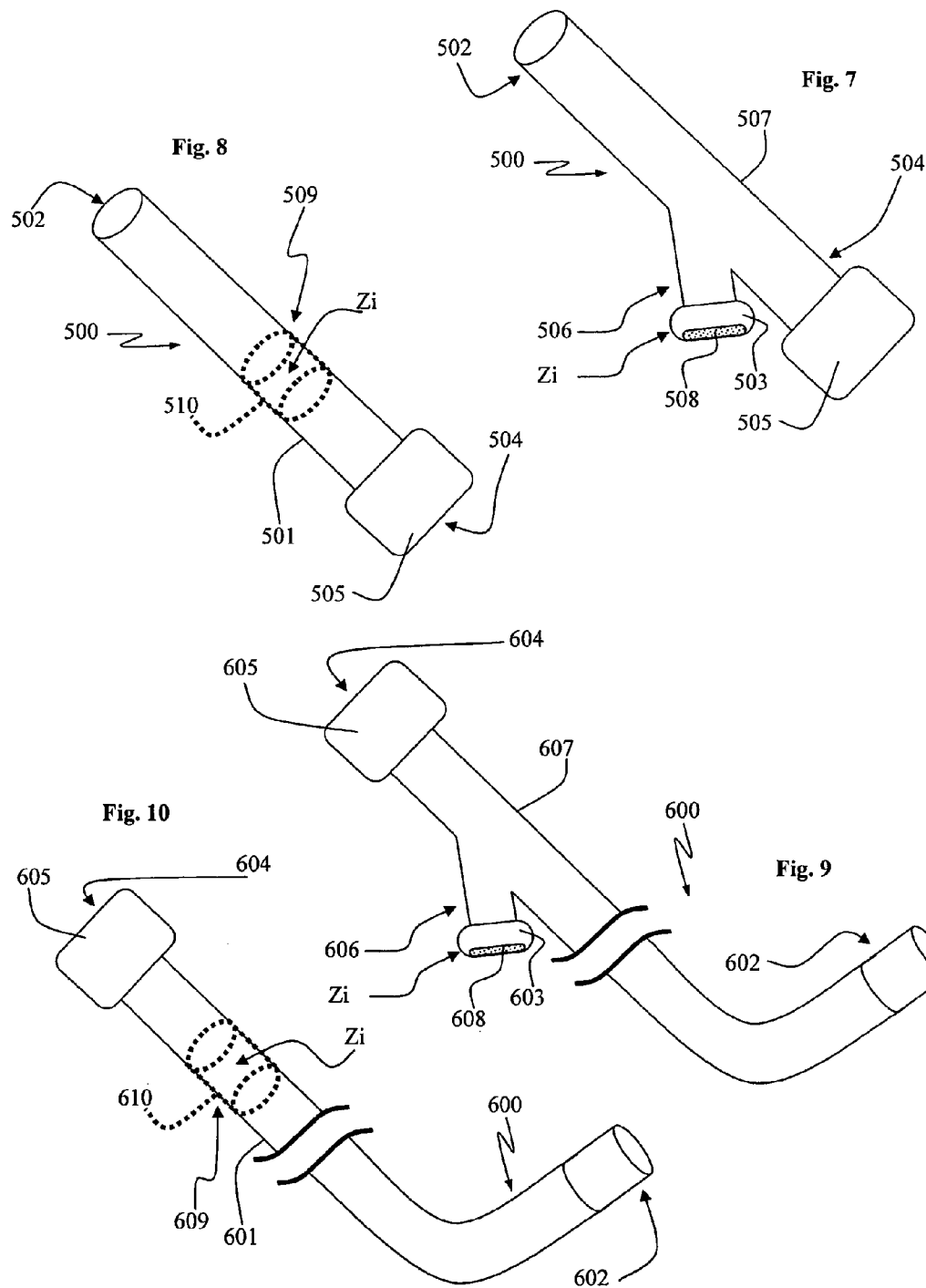

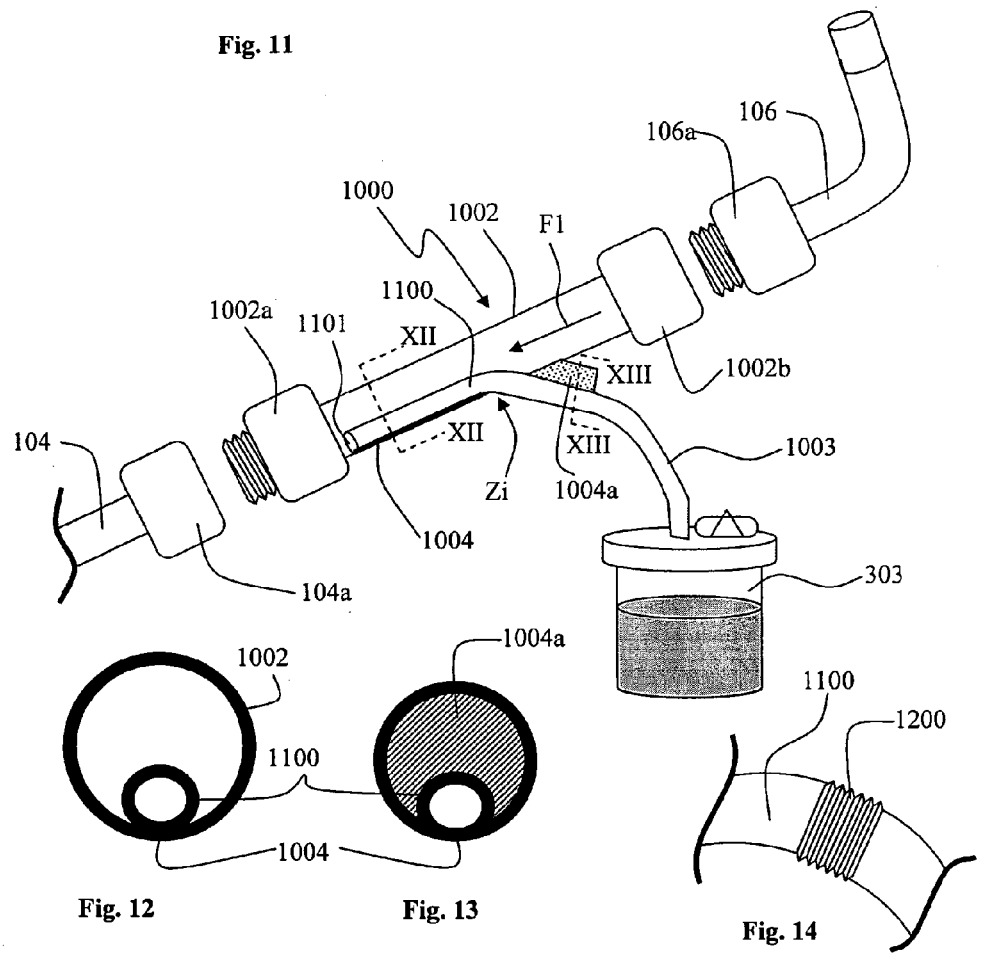
Fig. 11
Fig. 12  Fig. 13  Fig. 14
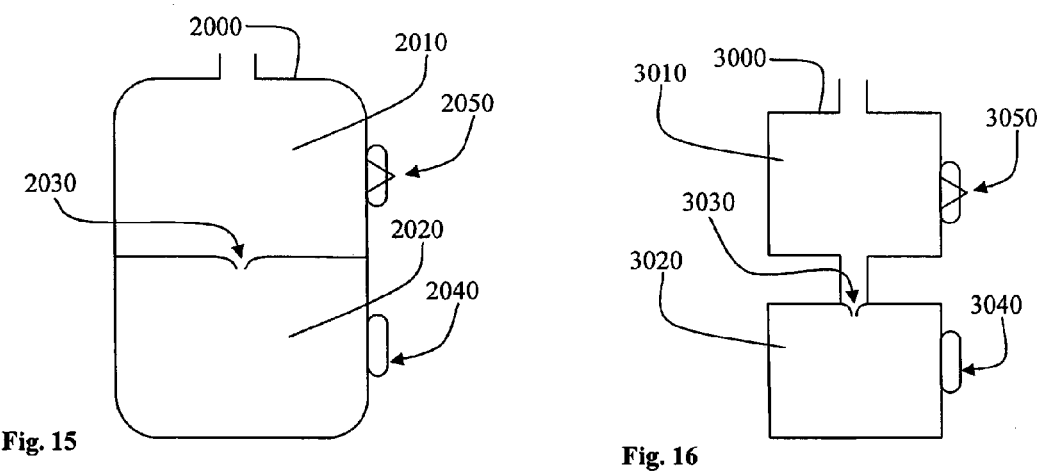
Fig. 15  Fig. 16

DEVICE FOR TAKING A SAMPLE OF A BODY FLUID AND METHOD FOR IMPLEMENTING SAME

FIELD OF THE INVENTION

The invention relates to a device for collecting a sample of body fluid, in particular blood, and to an implementation process.

BACKGROUND OF THE INVENTION

When a (human or animal) patient is perfused, it may be necessary to collect a sample from the patient, such as a blood sample, for analysis. In this case, an authorized person (doctor, nurse or veterinarian) performs:
- either a sample collection independent of the perfusion. The patient is therefore subjected to a first needle insertion for fitting the perfusion and then a second needle insertion for the sample collection;
- or a sample collection at the moment the catheter is put in place (or is changed), with a direct connection to the catheter, before putting the perfusion line in place;
- or a sample collection, using a syringe, from the stopcock ramp of the extension (customarily a few tens of cm long) inserted between the perfusion tubing and the catheter. In this case, it is necessary to perform a first purge operation (suction of between 1 and 7.5 ml depending on the practices and the type of blood analysis to be carried out) then to carry out the blood sample collection itself. The reinjection of the purge suction is in general carried out quite rapidly into the extension in order to avoid a risk of hemolysis.

The invention applies mainly, but not exclusively, to central or peripheral venous perfusions.

As is known, a perfusion in a peripheral vein is put in place in the following manner.

After having located a peripheral vein, the patient's skin is pierced using a needle covered with a catheter (such a device is known under the brand Cathlon®). Once the needle is positioned in a vein, the distal end of the catheter is pushed into the vein, the needle is removed, and the proximal end of the catheter is fastened to the patient's skin using a sterile dressing. Various diameters of catheter exist, and are generally expressed in terms of gauge (G). The diameter of the catheter used depends on the condition of the patient, on the operation to be carried out (sample collection or injection) and on the age of the patient. For example, the following catheters will be chosen: 22 to 24 gauge for newborns, 22 gauge for children from 1 month to 3 years old, 20 gauge for older children. For adults, it will be possible to choose catheters from 18 gauge (i.e. an external diameter of 1.1 mm to 1.3 mm) up to 14 gauge (i.e. an external diameter of 1.8 to 2.2 mm).

A table showing the connection between the "gauge" unit and the metric system is given below:

| Gauge (internal diameter of the needle) | External diameter (mm) |
| --- | --- |
| 24 G | 0.6 to 0.7 |
| 22 G | 0.7 to 0.9 |
| 20 G | 0.9 to 1.1 |
| 18 G | 1.1 to 1.3 |
| 16 G | 1.5 to 1.8 |
| 14 G | 1.8 to 2.2 |

The catheter bears, at its proximal end, a connection device, for example of Luer lock type, and at its distal end perfusion tubing. This connection device may be such that when the catheter is not connected, its proximal end is closed and the blood cannot escape.

In general, after connecting the catheter, a safety loop is produced with the tubing that is fastened to the patient's skin with tape. This safety loop prevents the catheter from being immediately pulled out in case of tension on the perfusion tubing.

The proximal end of the tubing is in fluid communication with an expansion vessel connected to a rigid or flexible bag of perfusion product attached to a pole. The latter must be high enough relative to the patient's catheter so that the perfusion product flows by simple gravity toward the catheter then the vascular system of the patient.

The tubing comprises, preferably, a toothed wheel for controlling the flow rate of perfusion, or other control system.

It is known to verify that the catheter is well positioned in the vascular system of the patient by detaching the perfusion bag from its pole and by lowering it to a height below that of the patient's catheter. Under these conditions, the blood pressure is greater than the pressure of the perfusion product. If the catheter is well positioned, it is possible to observe a reflux of blood into the perfusion tubing.

In order to avoid a second needle insertion into a perfused patient, document WO 2006/088771 proposes to equip a conventional perfusion with a reversible pump associated with control means. The latter is designed to intermittently interrupt the operation of the perfusion pump in the forward direction (that is to say from the bag of perfusion product toward the patient), in order to operate the pump in the rearward direction (that is to say from the patient to a sample collection circuit). In this way, it is possible to collect a sample of the patient's blood via the perfusion catheter.

However, this device requires meticulous control of the pump and a complex fluid circuit comprising multiple valves.

Moreover, this system may be noisy (due to the operation of the pump) and requires a source of energy for the collection of a sample of blood and the injection of the perfusion product.

SUMMARY OF THE INVENTION

A first objective of the invention is to propose a simple, effective and energy-efficient device that makes it possible to easily collect a sample of body fluid while avoiding another intrusion into the body of the patient, and while limiting the need for a purge prior to the sample collection.

Furthermore, when a (human or animal) patient is perfused, for example with a therapeutic product (saline solution, antibiotic solution, etc.), it may be necessary to give the patient a second perfusion of another product, such as blood, after the doctor has diagnosed a given medical situation (illness, accident, hemorrhage, etc.). In the example described, it is a need for blood.

In this case, an authorized person (doctor, nurse or veterinarian) must set up a second perfusion line, specific for the transfusion of blood.

Conventionally, for a peripheral venous route, the second perfusion is set up on the controlateral arm. The patient is therefore subjected to a first needle insertion for fitting the first perfusion, then a second needle insertion for fitting the second perfusion.

Before letting the product of the second perfusion flow, it is essential to carry out a final compatibility check between the treatment prescribed by the doctor and the treatment that is about to be given to the patient via the second perfusion.

For example, for blood transfusion, when a doctor has prescribed a transfusion for a patient of given blood group, the nurse must ensure that the blood bags that he/she has are compatible with the patient's blood group since there can be errors in allocating blood bags or in the identification of the patient or of the blood bags.

Conventionally, the nurse uses card stock impregnated with anti-A and anti-B reagent on which he/she deposits blood from the patient (obtained by pricking the end of the finger or a vein) and blood from a sample from the transfusion bag. For this purpose, the transfusion bags have a main container for the transfusion, and secondary sampling containers, that can be separated from the main container.

The nurse then assesses the presence of agglutinates on the card stock and compares the reactions obtained with the patient's blood and with the blood from the sample. The nurse must then apply the compatibility rules that he/she has learnt in order to interpret the results of the test. This interpretation may be tricky, especially in the presence of weak antigens or in certain pathologies.

Thus, it has been noticed that there are still many errors due to fatigue, due to an emergency situation or to inattention, during the interpretation of these tests, but also during the setting up of the transfusion bag and, more generally, of the second perfusion.

In particular, it has been noticed that only too often the product of the second perfusion is not that which had been prescribed by the doctor.

These errors may simply slow down the patient's recovery, for example when the dosage of the perfused product is lower than that which is prescribed by the doctor in order to cure the patient. They may also lead to the death of the patient, for example when the blood transfused is incompatible with the patient's blood group (A, B, AB or O), or when the patient is allergic to the antibiotic perfused whereas the patient was not allergic to the antibiotic initially prescribed.

Handling errors may also occur that are dangerous for the nursing staff if there is direct exposure to the patient's blood.

To overcome this problem, the current solutions aim to ensure that the information written on the transfusion bag and information written on a support borne by the patient agree. These technologies mainly consist of bar code or RFID chip control systems. However, handling errors still exist, especially due to perfusion bag labeling errors or patient identification errors.

Another objective of the present invention is therefore to propose a perfusion system that makes it possible to carry out, simply, effectively and energy-efficiently, a final compatibility check of a treatment, previously chosen by a doctor, with the patient and/or the medical situation previously diagnosed by a doctor.

For this, the invention proposes to produce a perfusion system comprising a final check on the same perfusion line connected to the patient.

For this purpose, one subject of the invention is a device for collecting a sample of a body fluid, such as blood, intended to be incorporated into a fluid circuit of a perfusion of a patient equipped with a perfusion catheter, and comprising a tubular structure for connection to the fluid circuit of the perfusion equipped:
  with a zone of intubation, in use, of a sample collection channel comprising a distal end; and
  with a means for holding, in use, in the tubular structure, the portion of the sample collection channel comprising a distal end, so that said distal end is pointed toward the perfusion catheter, in the flow direction of the perfusion product, from a container of perfusion product to the perfusion catheter.

According to other embodiments:
  the portion comprising the distal end of the sample collection channel may be fixed in the tubular structure, and a portion comprising a proximal end of the sample collection channel emerges outside of the tubular structure level with the intubation zone;
  the intubation zone may comprise an insertion means suitable for enabling, in use, the insertion, into the tubular structure, of the portion of the sample collection channel comprising the distal end;
  the intubation zone may be arranged so that, in use, it is positioned at a given maximum vertical distance from the proximal end of the catheter;
  the given maximum vertical distance may be between 0 cm and 50 cm;
  the insertion means may be chosen from:
    a membrane made of a leaktight material that retains its leaktightness after having been pierced; and
    a leaktight connector;
  the leaktight material that retains its leaktightness after having been pierced may be chosen from a silicone polymer, such as polydimethylsiloxane (PDMS), polymethyl methacrylate (PMMA), polyvinyl chloride (PVC) and Tygon®; and/or
  the sample collection device may comprise, in addition:
    a means of connection to a proximal end of a perfusion catheter, and
    a means of connection to a distal end of a perfusion tubing.

The invention also relates to a perfusion catheter comprising:
  a distal end intended to be inserted into a patient;
  a proximal end intended to be connected with a distal end of a perfusion tubing;
and comprising, between the distal end and the proximal end, a preceding device for collecting a sample of body fluid, arranged so that, in use, the intubation zone is positioned at a given maximum vertical distance from the proximal end of the catheter.

The invention also relates to a perfusion tubing comprising:
  a proximal end intended to be connected to a container of a first perfusion product;
  a distal end intended to be connected with a proximal end of a perfusion catheter inserted into a patient;
and comprising, between the proximal end and the distal end, a preceding device for collecting a sample of body fluid, arranged so that, in use, the intubation zone is positioned at a given maximum vertical distance from the proximal end of the catheter.

The invention also relates to a kit for collecting a sample of a body fluid, comprising:
  a sample collection channel comprising a proximal end intended to be connected to a sample collection container, and a distal end; and
  a preceding sample collection device.

According to other embodiments:
  the kit may have a ratio between the internal diameter of the sample collection channel and the external diameter of the tubular structure of the sample collection device of less than 1, typically between $1/20$ and $1/3$;

the sample collection channel may have a length between its two ends of between 10 cm and 100 cm, preferably between 20 cm and 50 cm;

the kit may comprise, in addition, a means for analyzing the collected body fluid;

the analysis means may also be capable of analyzing a sample of given product and of comparing the collected body fluid and the sample of given product;

the analysis means may comprise a reaction chamber and a detection means;

the kit may comprise, in addition, a means for controlling the flow of a second perfusion, the analysis means being capable of transmitting, to the flow control means, comparison information of the collected body fluid and the sample of given product;

the kit may comprise a means for displaying the comparison information of the collected body fluid and the sample of given product;

the analysis means may be capable of controlling the flow control means so that it blocks the flow of the product of the second perfusion if the body fluid and the product of the second perfusion are incompatible, and so that it permits the flow of the product of the second perfusion if the body fluid and the product of the second perfusion are compatible;

the analysis means may be capable of controlling the flow control means so that it automatically generates the flow of the product of the second perfusion if the body fluid and the product of the second perfusion are compatible, and so that it does not generate the flow of the product of the second perfusion if the body fluid and the product of the second perfusion are incompatible;

the kit may comprise, in addition, a sample collection container, optionally comprising a blood anticoagulant means;

the sample collection container may be a container having two compartments separated by a non-return system, such as a valve, a flap, a ball, a float, etc.;

the sample collection container may be a container that can be deformed and actuated mechanically, for example manually, such as an evacuator-aspirator bulb;

the sample collection container may be put under vacuum beforehand and kept in this state by a clamp;

the kit may comprise a preceding perfusion catheter, equipped with the sample collection device; and/or the kit may comprise a preceding perfusion tubing, equipped with the sample collection device.

The invention also relates to a process for implementing a preceding sample collection kit, comprising the following steps:

incorporating the sample collection device into a fluid circuit of a perfusion previously fitted to a patient equipped with a perfusion catheter, in an external portion of the fluid circuit relative to the body of the patient;

holding, inside the tubular structure, the portion of the sample collection channel comprising the distal end, so that said distal end is pointed toward the perfusion catheter, in the flow direction of the perfusion product, from a container of perfusion product to the perfusion catheter;

bringing the sample collection container to a height below that of the catheter of the patient, so that the body fluid flows into the sample collection channel, countercurrent compared to the perfusion product, then toward the sample collection container; and holding the sample collection container at a height below that of the catheter of the patient for a sufficient time to obtain, in the sample collection container, a volume sufficient to constitute a collection of a sample of body fluid.

This process makes it possible to collect a sample of body fluid without having to perform an additional needle insertion into an already perfused patient.

The positioning of the perfusion catheter in the body of the patient is not part of the present invention. On the contrary, the invention makes it possible to take advantage of the fitting or changing of a perfusion already fitted to a patient in order to collect a sample of body fluid, such as blood, and to avoid another intrusion into the body of the patient.

According to other embodiments:

the process may comprise a step of inserting, via the insertion means, the distal end of the sample collection channel into the tubular structure of the sample collection device, so that said distal end is pointed toward the perfusion catheter, in the flow direction of the perfusion product;

the sample collection device may be arranged so that, in use, the intubation zone is positioned at a given maximum vertical distance from the proximal end of the catheter;

the given maximum vertical distance may be between 0 cm and 50 cm;

the distal end of the sample collection channel may be arranged at a given distance from a proximal end of the perfusion catheter, said distance being referred to as the "butt-joining distance" and being between 0 cm and 20 cm, preferably between 0 cm and 3 cm;

the process may comprise, in addition, a step of placing the sample collection container in fluid communication with a means of analyzing the collected body fluid, and a step of analyzing the collected body fluid;

the process may comprise, in addition, a step of analyzing and comparing a sample of given product and the collected body fluid;

the process may comprise, in addition, a step of generating comparison information of the collected body fluid and the sample of given product;

the process may comprise, in addition, a step of placing a second perfusion of given product in fluid communication with the fluid circuit of the first perfusion;

the process may comprise, in addition, a step of transmitting, to a means for controlling the flow of the product of the second perfusion, the comparison information of the collected body fluid and the sample of given product;

the process may comprise, in addition, a step of displaying comparison information of the collected body fluid and the sample of given product;

the process may comprise, in addition, a step of permitting the flow of the product of the second perfusion if the comparison information indicates that the body fluid and the product of the second perfusion are compatible, and of blocking the flow of the product of the second perfusion if the comparison information indicates that the body fluid and the product of the second perfusion are incompatible; and/or the process may comprise, in addition, a step of automatically generating the flow of the product of the second perfusion if the comparison information indicates that the body fluid and the product of the second perfusion are compatible, and of blocking the flow of the product of the second perfusion if the comparison information indicates that the body fluid and the product of the second perfusion are incompatible.

BRIEF DESCRIPTION OF THE DRAWINGS

Other features of the invention will be set out in the detailed description below, made with reference to the appended figures that represent, respectively:

FIG. 1, a schematic plan view of a first embodiment of a sample collection device according to the invention, installed in a first manner in the fluid circuit of a perfusion of a patient;

FIG. 2, a partial enlargement of FIG. 1 illustrating, in detail, the sample collection device according to the invention;

FIG. 3, a schematic plan view of a second embodiment of a sample collection device according to the invention installed in the fluid circuit of a perfusion of a patient;

FIG. 4, a partial enlargement of FIG. 3 illustrating, in detail, the sample collection device according to the invention;

FIG. 5, a schematic plan view of the first embodiment of a sample collection device according to the invention installed in a second manner in the fluid circuit of a perfusion of a patient;

FIG. 6, a partial enlargement of FIG. 3 illustrating, in detail, the sample collection device according to FIG. 5;

FIGS. 7 and 8, schematic plan views of two embodiments of a perfusion catheter according to the invention;

FIGS. 9 and 10, schematic plan views of two embodiments of perfusion tubing according to the invention;

FIG. 11, a schematic plan view of another embodiment of a sample collection device according to the invention, in which the tubular structure includes a portion of the sample collection channel;

FIGS. 12 and 13, schematic cross-sectional views of the embodiment from FIG. 11;

FIG. 14, a partial schematic plan view of an embodiment of the sample collection channel;

FIGS. 15 and 16, schematic views of two embodiments of a sample collection container according to the invention;

FIG. 19, a schematic plan view of a third embodiment of one particular use of the sample collection device according to the invention.

DETAILED DESCRIPTION OF THE INVENTION

Figure 17:
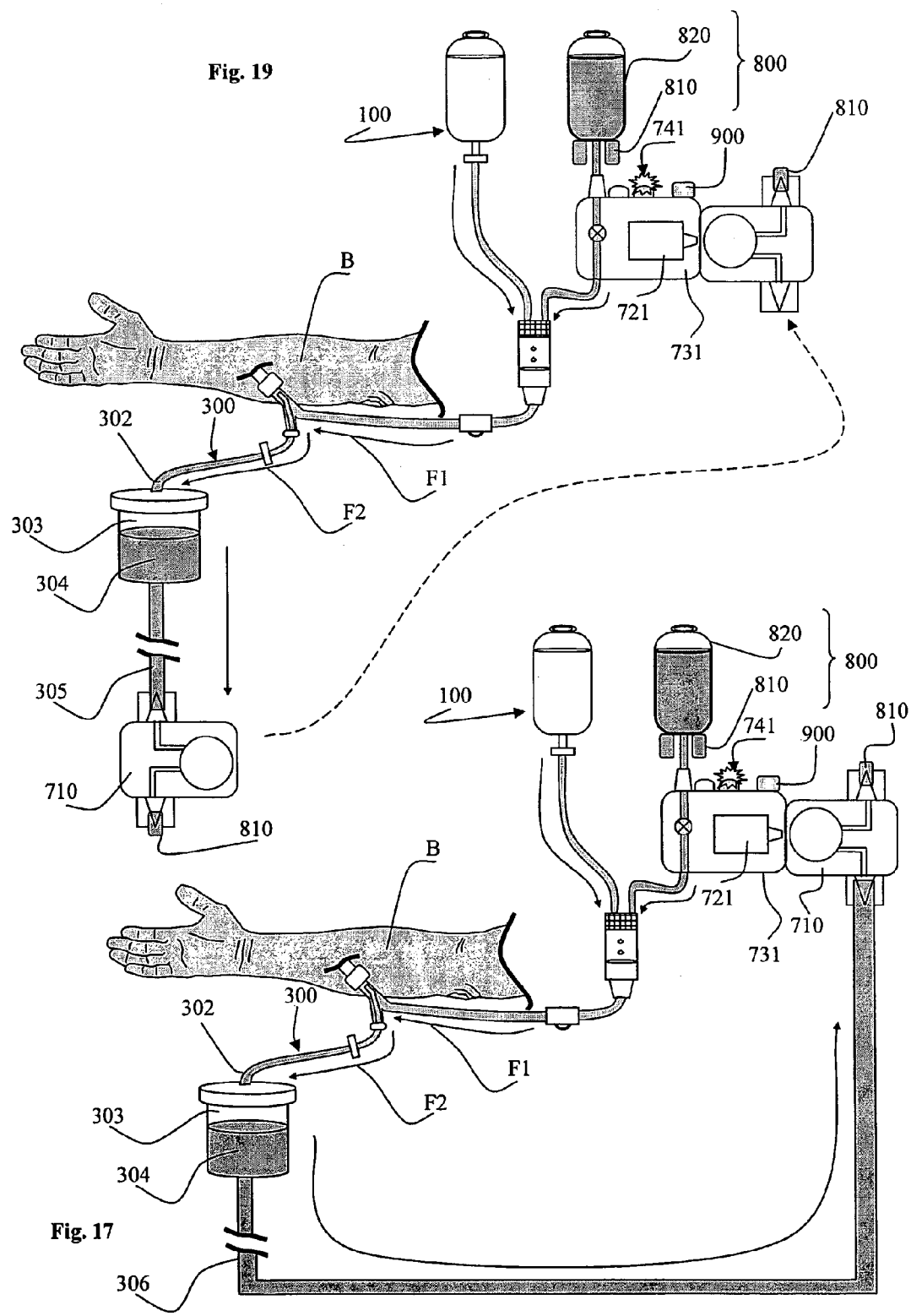
FIG. 17, a schematic plan view of a first embodiment of one particular use of the sample collection device according to the invention.

The present description relates to blood sample collection. However, any body fluid could be collected as a function of the prior fitting of the perfusion to the patient (urine, cerebrospinal fluid, pleural fluid, ascites fluid, peritoneal fluid, etc.).

FIG. 1 represents the arm B of a patient equipped with a perfusion 100. Such a perfusion is conventionally constituted of a container 101 of perfusion product 102, in fluid communication with a perfusion catheter 104 via tubing 106. Generally, a filter 108 and an expansion vessel 110 are provided within the fluid circuit of the perfusion. A toothed wheel 112 for adjusting the flow rate of the perfusion product 102 is also provided.

In all of the structures described subsequently, stopcocks or clamps may be provided to permit or prohibit the flow of various products.

The positioning of the perfusion catheter in the body of the patient, and the fitting of the perfusion in general are not part of the present invention.

Indeed, the fluid sample collection device according to the invention is intended to be incorporated, not into a patient, but into the fluid circuit of the perfusion previously fitted to a patient, between the catheter and the perfusion container, in an external portion of the fluid circuit relative to the body of the patient.

The device 200 according to the invention comprises a tubular structure 202 of fluid connection to the fluid circuit of the perfusion 100. This tubular structure 202 is equipped with a zone Zi of intubation, in use, of a sample collection channel 300 comprising a distal end 301.

This tubular structure is also equipped with a holding means 203. This is suitable for enabling, in use, the holding, in the tubular structure, of the portion of the sample collection channel 300 comprising a distal end 301, so that the distal end 301 of the sample collection channel 300 is pointed toward the perfusion catheter 104, in the flow direction F1 of the perfusion product 102, from a container 101 of perfusion product to the perfusion catheter 104.

The term "holding" should be understood in the broad sense. It relates, on the one hand, to a reversible holding of the portion of the sample collection channel inserted in the tubular structure. In this case, the device according to the invention does not comprise a sample collection channel. This must be inserted by the user, during the sample collection, into the tubular structure (see FIGS. 1 to 6 and 17 to 19).

The term "holding" also relates to a permanent holding in the tubular structure, of the portion of the sample collection channel so that it only forms one and the same part comprising two tubes. In this way, in use, a portion of the sample collection channel 300 is arranged in the tubular structure so that the distal end 301 of the sample collection channel 300 is pointed toward the perfusion catheter 104, in the flow direction F1 of the perfusion product 102, from a container 101 of perfusion product to the perfusion catheter 104 (see FIGS. 11 to 13).

In the embodiments from FIGS. 1 to 6 and 17 to 19, the intubation zone Zi comprises an insertion means 204.

In the embodiment from FIG. 1, the tubular structure 202 is a Y connection system having a branch intended to be in fluid communication with the tubing 106 of the perfusion 100, and a branch equipped with an intubation zone Zi bearing a holding means 203 and a membrane 204 for the leaktight insertion of the channel 300. This membrane is made of a leaktight material that retains its leaktightness after having been pierced. Alternatively, the structure of the membrane (thickness and/or stiffness) and its arrangement in the Y system may be such that the sample collection channel is both inserted and held in the usage position, that is to say inside the tubular structure 202. In this case, the membrane carries out the roles of a holding means and an insertion means.

The leaktight material that retains its leaktightness after having been pierced is chosen from a silicone polymer, such as polydimethylsiloxane (PDMS), polymethyl methacrylate (PMMA), polyvinyl chloride (PVC), and Tygon® (manufactured by the company Saint-Gobain), etc.

The sample collection channel 300 comprises a distal end 301, which has a stiffness sufficient to pierce the membrane 204, and a proximal end 302 intended to be in fluid communication with a sample collection container 303. In the entire remainder of the present description, the containers used for collecting the liquid sample advantageously have a closeable air inlet.

According to one variant that is not illustrated, the holding means is a leaktight connector, for example of Luer lock type. In this case, the channel 300 is equipped with a corresponding Luer lock connector, into which passes, in a leaktight manner, the portion of the channel bearing the distal end 301. The association of the Luer lock connectors enables the insertion of the sample collection channel into the tubular structure and holds the portion of the channel bearing the distal end 301 pointed toward the perfusion catheter 104, in the flow direction F1 of the perfusion product 102, from a container 101 of perfusion product to the perfusion catheter 104.

Thus, the distal end 301 of the sample collection channel 300 remains located outside of the perfusion catheter and, therefore, outside the body of the patient.

It is therefore an ex vivo installation of the sample collection channel in a fluid circuit of a perfusion located outside of the body of the patient. It is not an in vivo installation, that is to say in the body of the patient.

The implementation process will be described further on.

The second embodiment 400 of a liquid sample collection device according to the invention, illustrated in FIG. 2, comprises a tubular structure 402 for connection to the fluid circuit of the perfusion 100 equipped with an intubation zone Zi comprising a means 404 for insertion, into the tubular structure 402, of a portion of a sample collection channel 300.

In this embodiment, the insertion means 404 is a membrane made of a leaktight material that retains its leaktightness after having been pierced. This membrane 404 may occupy all or part of the wall of the tubular structure 402. This membrane 404 has a structure (thickness and/or stiffness and/or material and/or arrangement) that enables it to carry out both the role of holding means and the role of insertion means. In other words, the sample collection channel 300 is inserted and held in the usage position, that is to say inside the tubular structure 402, the distal end 301 of the sample collection channel 300 being pointed toward the perfusion catheter 104, in the flow direction F1 of the perfusion product, from the container 101 of perfusion product 102 to the perfusion catheter 104. Alternatively, the tubular structure may comprise a holding means independent of the membrane which then would only be used for the insertion.

The leaktight material that retains its leaktightness after having been pierced is chosen from a silicone polymer, such as polydimethylsiloxane (PDMS), polymethyl methacrylate (PMMA), polyvinyl chloride (PVC), Tygon® (manufactured by the company Saint-Gobain), etc.

The collection of a sample of body fluid, illustrated in FIGS. 1 to 6 and 17 to 19, is carried out in the following manner.

When collection of a sample of body fluid is necessary, here blood, the sample collection device 200-400 according to the invention is incorporated into a fluid circuit of a perfusion 100 previously fitted to a patient B.

This incorporation is carried out in the vicinity of the proximal end 104a of the perfusion catheter 104 and is not therefore carried out directly in the patient, but in an external portion of the fluid circuit relative to the body of the patient.

It is not therefore necessary to carry out an additional needle insertion into the patient. No direct surgical intervention on the patient is necessary for putting into place the device according to the invention, nor for the implementation thereof.

In a second step, via the insertion means 204-404 of the sample collection device 200-400, the distal end 301 of the sample collection channel 300 is inserted into the tubular structure 202-402 of the sample collection device, so that said distal end 301 is pointed toward the perfusion catheter 104, in the flow direction F1 of the perfusion product. The distal end 301 of the sample collection channel 300 remains located outside of the perfusion catheter 104 and, therefore, outside of the patient.

Next, the perfusion tubing 106 is clamped, then the sample collection channel 300 is unclamped and the sample collection container 303 is brought to a height $H_C$ below the height $H_{cat}$ of the catheter of the patient. Advantageously, the sample collection channel and the container are brought to atmospheric pressure owing to the closeable air inlet of the container.

Surprisingly, this enables the blood to flow into the sample collection channel 300, countercurrent along the direction of the arrow F2, relative to the perfusion product which is located between the catheter and the clamp of the tubing 106. The perfusion product located above the sample collection channel and below the clamp of the tubing 106 is not collected at the same time as the blood.

Moreover, it is noticed that it is not necessary to lower the perfusion container 101 in order for the blood to flow into the sample collection channel.

When the blood flows into the sample collection channel 300, the sample collection container 303 is held in this position for a sufficient time to obtain, in the sample collection container 303, the desired sample collection volume 304.

In order to obtain a flow of blood under good conditions (flow rate, comfort of the patient, etc.), the intubation zone Zi of the sample collection device is preferably arranged so that, in the usage position, it is positioned at a given maximum vertical distance $Dv_{max}$ from the proximal end of the catheter 104. The vertical direction is the direction of the gravitational field.

The vertical distance Dv is defined as the distance between the height $H_{Zi}$ of the intubation zone Zi and the height $H_{cat}$ of the perfusion catheter on the height scale H.

The maximum vertical distance $Dv_{max}$ is less than 50 cm. Preferably, it is between −50 and 50 cm (the negative sign means that the intubation zone is below the proximal end of the catheter).

In FIGS. 1 and 3, the intubation zone Zi is located below the end of the perfusion catheter 104. The vertical distance, denoted respectively by Dv1 and Dv2, is therefore negative. This arrangement is optimal for obtaining blood flow.

However, in practice, it may happen that the perfusion catheter 104 is located below the intubation zone Zi. This situation, illustrated in FIG. 5, may happen, for example, when the perfusion device according to the invention is positioned in the safety loop or in an intermediate tubing with a multiple connection zone. In this case, the vertical distance Dv5 is positive.

In order to obtain a flow of blood, the distance Dv5 must remain smaller than the given maximum vertical distance $DV_{max}$.

In practice, and generally, the sample collection device is incorporated into a fluid circuit of the perfusion in the vicinity of the perfusion catheter, that is to say so that the intubation zone is positioned at a distance of between 0 and 50 cm, preferably between 5 cm and 15 cm.

In this way, during use, the intubation zone has little risk of being above the proximal end of the catheter, at a vertical distance greater than the given maximum vertical distance $DV_{max}$.

At the very start of the sample collection (transient state), the fluid collected is constituted by a mixture of blood and of the perfusion product located between the vascular system of the patient and the distal end 301 of the sample collection channel 300.

It may therefore be preferable to only connect the sample collection container 303 when the blood appears pure (visually, or by any means of analysis).

Alternatively, the volume of perfusion product between the vascular system of the patient and the distal end 301 of the sample collection channel 300 may be known owing to the dimensions of the catheter and to the measurement of the distance $D_{c1}$ referred to as the "butt-joining distance" between the proximal end 104a of the catheter 104 (determining the origin $d_0$ of the distance mark D on FIGS. 1 and 2) and the distal end 301 of the channel 300. It is therefore possible to calculate the dilution ratio of the blood collected in the container 303.

According to another embodiment, a container 2000 may be provided that has two compartments 2010 and 2020 separated by a non-return system, such as a valve 2030, a flap, a ball, a float, etc. (see FIG. 15). According to one variant, the two compartments 3010 and 3020 of the container 3000 are mounted independently in series and are separated by a non-return system 3030 (see FIG. 16). In the two examples illustrated, the compartment 2020 or the compartment 3020 furthest downstream must allow the storage of a quantity of body fluid equal to, or slightly greater than, the volume of perfusion product located between the vascular system of the patient and the distal end 301 of the sample collection channel 300. During this storage, the air is evacuated by an air evacuation valve 2040-3040.

When the compartment 2020 or the compartment 3020 furthest downstream is full, the compartment 2010 or the compartment 3010 upstream is filled. The non-return systems 2030-3030 prevent this diluted fluid, located in the compartment furthest downstream, from mixing with the "pure" fluid which is stored in the upstream compartment.

A subsequent analysis could therefore be preferably carried out on the pure fluid. For this purpose, the containers from FIGS. 15 and 16 have a valve 2050-3050 for air evacuation and for connection to a means of analyzing the collected body fluid (not represented in these figures).

The distal end 301 of the sample collection channel 300 is inserted at a given butt-joining distance from a proximal end of the perfusion catheter.

In order to know this distance and optimize the sample collection, the tubular structure of the sample collection device according to the invention preferably has a graduation expressed in terms of distance.

Advantageously, this graduation may be directly expressed in terms of volume from the distal end of the catheter in contact with the patient's vascular system. This enables an easier calculation of the dilution ratio of the sample collection.

Experimentally, it has been determined that the optimal butt-joining distance $d_{Copt}$ is between 0 and 20 cm, preferably between 0 and 3 cm.

Thus, at a butt-joining distance $d_{C2}$, the sample collection is of poor quality: it is too long or it comprises perfusion product.

The butt-joining distance, the diameter $D_C$ and the length of the sample collection channel are suitable for enabling a sample collection of optimal quality, while ensuring that the sample collection time does not exceed one minute approximately, preferably ten seconds. This time is considered, in practice, to be the maximum time that is comfortable for the patient.

In the embodiments from FIGS. 1 to 6 and 17 to 19, when the amount collected is sufficient, it is possible to deactivate the holding means, withdraw the sample collection channel out of the tubular structure and seal the insertion means in a leaktight manner (automatically or manually).

Advantageously, to avoid, for example during poor handling, a return of blood from the collection channel toward the fluid circuit of the perfusion, the distal end 301 of the sample collection channel 300 is equipped with a non-return means 305 such as a non-return valve of duckbill or tricuspid type. Alternatively, the non-return means may also be located at the proximal end of the sample collection channel 300.

The sample collection device according to the invention may be incorporated into the fluid circuit of the perfusion between the perfusion catheter and the perfusion tubing. For this, the sample collection device comprises:
  a means for connection to a proximal end of the perfusion catheter, and
  a means for connection to the distal end of the perfusion tubing.

In order to install this device, the operator connects the device to the distal end of the perfusion tubing, purges the whole of the tubing of air and connects the device to the proximal end of the perfusion catheter.

The connection means may be of Luer lock type.

It may be envisaged to provide a catheter or perfusion tubing that is pre-equipped, during its manufacture, with a sample collection device according to the invention.

Thus, as shown in FIGS. 7 and 8, a perfusion catheter 500 according to the invention comprises:
  a distal end 502 intended to be inserted into a patient;
  a proximal end 504 intended to be connected, for example via a Luer lock connector 505, with a distal end of a perfusion tubing; and
  between the distal end 502 and the proximal end 504, a device 506-509 for collecting a sample of body fluid according to the invention, arranged so that, in use, the intubation zone Zi is positioned at a given maximum vertical distance $Dv_{max}$ from the proximal end of the catheter.

This arrangement enables a good flow of the body fluid during use. The given maximum vertical distance $Dv_{max}$ is between 0 cm and 50 cm.

In these figures, the needle for perforating the catheter has not been represented.

In the embodiment from FIG. 7, the device 506 has a tubular structure 507 which is a Y connection system comprising a holding means 503 equipped with an insertion membrane 508 made of a leaktight material that retains its leaktightness after having been pierced. This tubular structure is similar to that which was described in connection with FIGS. 1 and 2.

In the embodiment from FIG. 8, the device 509 has a tubular structure 501 equipped with a membrane 510 made of a leaktight material that retains its leaktightness after having been pierced. This membrane 510 has a structure (thickness and/or stiffness and/or material and/or arrangement) that enables it to carry out both the role of holding means and the role of insertion means. This membrane 510 is similar to that which was described in connection with FIGS. 3 and 4.

Thus, when the perfusion is put in place with this catheter according to the invention, the sample collection device according to the invention is incorporated into the fluid circuit of the perfusion between the perfusion catheter and the perfusion tubing.

Similarly, as shown in FIGS. 9 and 10, a perfusion tubing 600 according to the invention comprises:
- a proximal end 602 intended to be connected to a container of a first perfusion product;
- a distal end 604 intended to be connected, for example via a Luer lock connector 605, with a proximal end of a perfusion catheter inserted into a patient; and
- between the proximal end 602 and the distal end 604, a device 606-609 for collecting body fluid according to the invention, arranged so that, in use, the intubation zone is positioned at a given maximum vertical distance $Dv_{max}$ from the proximal end of the perfusion catheter.

This sample collection device is, preferably, arranged as close as possible to the distal end 604, so that, in the usage position, the intubation zone is positioned at a distance between 0 cm and 50 cm, preferably between 5 and 15 cm.

In the embodiment from FIG. 9, the device 606 has a tubular structure 607 which is a Y connection system comprising a holding means 603 equipped with an insertion membrane 608 made of a leaktight material that retains its leaktightness after having been pierced. This tubular structure is similar to that which was described in connection with FIG. 1.

In the embodiment from FIG. 10, the device 609 has a tubular structure 601 equipped with a membrane 610 made of a leaktight material that retains its leaktightness after having been pierced. This membrane 610 has a structure (thickness and/or stiffness and/or material and/or arrangement) that enables it to carry out both the role of holding means and the role of insertion means. This membrane 610 is similar to that which was described in connection with FIG. 3.

Thus, when the perfusion is put in place, with this tubing according to the invention, the sample collection device according to the invention is incorporated into the fluid circuit of the perfusion between the perfusion catheter and the perfusion tubing.

With a catheter or tubing integrating, from manufacture onwards, a sample collection device according to the invention, it is not necessary to temporarily stop the perfusion in order to incorporate the sample collection device according to the invention.

The implementation of the process described previously may be carried out with a kit for collecting a sample of a body fluid comprising a sample collection device illustrated in FIGS. 1 to 6, and a sample collection channel 300 having a distal end and a proximal end intended to be connected to a sample collection container. Of course, the kit may comprise, in addition, the sample collection container.

In a first embodiment, the sample collection kit according to the invention may comprise a sample collection channel and a perfusion catheter equipped with the sample collection device, such as those which are represented in FIGS. 7 and 8. Owing to such a kit, the procedures for installing the perfusion are not modified.

In a second embodiment, the sample collection kit according to the invention may comprise a sample collection channel and a perfusion tubing equipped with the sample collection device according to the invention, such as those which are represented in FIGS. 9 and 10. Owing to such a kit, the procedures for installing the perfusion are not modified.

Another embodiment of a sample collection device 1000 according to the invention is illustrated in FIG. 11. It comprises a tubular structure 1002 for connection to the fluid circuit of the perfusion represented, in this FIG. 11, by a catheter 104 and tubing 106. For this purpose, the tubular structure 1002, the catheter 104 and the tubing preferably have Luer lock connections, respectively 1002*a*, 1002*b*, 104*a* and 106*a*.

The sample collection device 1000 also comprises a holding means 1004 suitable for enabling, in use, the holding, inside the tubular structure 1002, of a portion of a sample collection channel 1100 comprising a distal end 1101. In this way, in use, the distal end 1101 of the sample collection channel 1100 is pointed toward the perfusion catheter 104, in the flow direction F1 of the perfusion product.

The portion of the sample collection channel 1100 comprising the distal end 1101 is therefore directly incorporated into the tubular structure 1002, and a portion 1003 of the sample collection channel 1100 comprising a proximal end emerges outside of the tubular structure level with the intubation zone Zi.

The holding means 1004 is here constituted by the mechanical connection between the channel 1100 and the tubular structure. As shown in FIGS. 12 and 13, which are transverse cross sections of FIG. 11, the channel 1100 and the tubular structure 1002 constitute one and the same part. The holding means may be a longitudinal weld.

The distal end of the sample collection channel is arranged at a given butt-joining distance from the proximal end of the perfusion catheter, of between 0 cm and 20 cm, preferably between 0 cm and 3 cm. This distance cannot be adjusted by the nursing staff, but is predefined during the manufacture of the device. This enables easier handling while avoiding an additional technical gesture on the part of the nursing staff.

In FIG. 11, the holding means comprises, optionally, a solid part 1004*a* resembling the Y branch of the embodiments from FIGS. 1 and 2. This solid part makes it possible to partially support the portion 1003 emerging from the tubular portion 1002 and, thus, to avoid folding of the channel 1100. This solid part may be located above, below or all around the sample collection channel.

A sample collection device according to the invention that directly incorporates a portion of the sample collection channel prevents the user from having to insert the channel into the tubular structure. Specifically, this insertion is a medical gesture that may not be carried out satisfactorily, for example if the butt-joining distance is too large. Moreover, the insertion may lead to a folding of the channel which prevents the flow of the body fluid to the container 303.

To avoid this folding phenomenon, the sample collection channel 1100 may comprise at least one accordion structure (see FIG. 14) enabling it to bend without forming folds.

This accordion structure 1200 may equip the sample collection channel of all the embodiments of the device according to the invention.

In all the preceding sample collection devices or kits, the ratio between the diameter Dc of the sample collection channel and the diameter Dt of the tubular structure of the sample collection device is, preferably, less than 1, and typically between ⅟20 and ⅓. This makes it possible to ensure the continuity of the supply of perfusion product in spite of the blood sample collection.

Similarly, the external diameter of the perfusion catheter is, preferably, between 14 G (gauge) and 24 G, advantageously between 14 G and 18 G.

The larger this diameter, the greater the sample collection flow rate may be. By playing with the height of the container relative to the patient's catheter, it is possible to adjust the flow rate and increase the throughput. The sample collection can therefore be carried out in a time that is comfortable for the patient, of one minute or less, preferably approximately ten seconds.

Preferably, the sample collection channel has a length between its two ends of between 10 cm and 100 cm, advantageously between 20 cm and 50 cm.

The sample collection device according to the invention may advantageously be used to produce a system of secure perfusion, such as secure blood transfusion.

Figure 18:
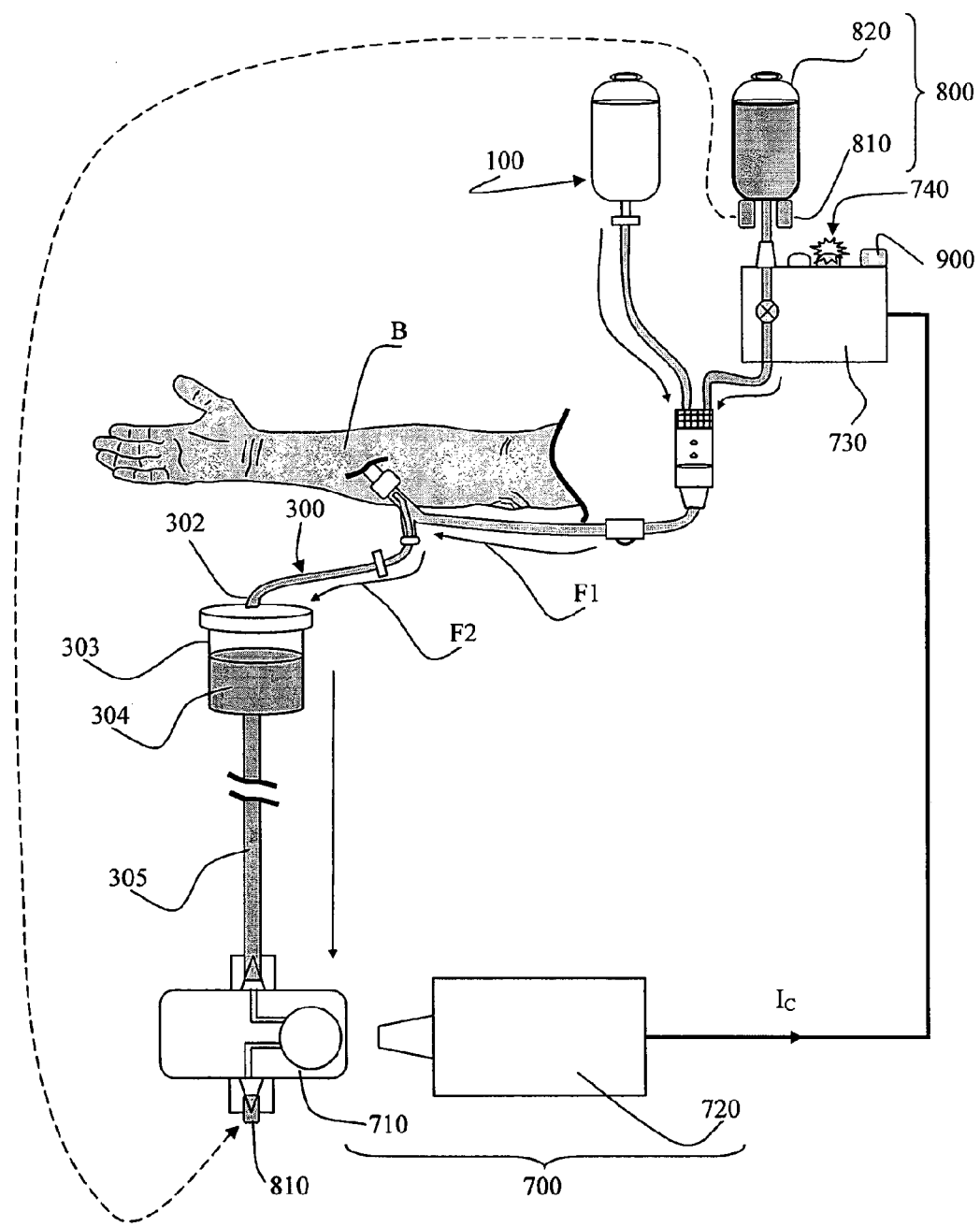
FIG. 18, a schematic plan view of a second embodiment of one particular use of the sample collection device according to the invention.

This system and the implementation thereof are illustrated in FIGS. 17 to 19 described below.

Thus, the process for implementing the device according to the invention may comprise, in addition, a step of placing the sample collection container 303 in fluid communication, via a line 305, with a means 700 of analyzing the collected body fluid 304, then a step of analyzing this fluid 304. This analysis means 700 may be included in a kit for collecting a sample of a body fluid according to the invention.

In the embodiment from FIG. 17, the analysis means 700 comprises a reaction chamber 710 and a detection means 720.

The reaction chamber 710 may have any form suitable for the reaction that must be detected.

One exemplary embodiment of a reaction chamber is a cassette comprising a biochip provided with a fluid circuit.

One particularly advantageous example, within the context of a secure blood transfusion system, is the use of biofunctionalized gold biochips 710 in combination with a detection device 720 based on optical transductions (such as those sold by the company GE Healthcare under the name "BIAcore system").

Based on surface plasmon resonance, this type of device measures a variation of the resonance extinction angle (dependant on a variation of refractive index at the gold/dielectric interface) which may be correlated to a variation in mass.

Carried out on a glass support provided with a thin layer of gold, the functionalization takes place in two steps. A first step enables the reconstitution of an organic thin film having certain activatable chemical functions (of the type: SH, COOH, $NH_2$, etc.) for the subsequent grafting of antibodies. During the second step, this layer is activated and the antibodies deposited at its surface are immobilized.

The inventors have discovered that after chemical treatment of the gold surface, the immobilization of the anti-A and anti-B antibodies of IgM type was significantly improved at a pH of around 4.65.

Under these pH conditions, the degree of grafting reaches on average 1500 IgM/$\mu m^2$ which makes it possible to involve up to 100 000 antibodies per red corpuscle captured.

This leads to a strong interaction between the erythrocytes and the immunosensor having a surface functionalized by anti-A and anti-B IgMs, even after several rinses.

Thus, the means 700 is capable of analyzing the collected body fluid 304 by interpreting the detection information, resulting from the detection means 720, relating to interactions between the corpuscles of the blood and the antibodies present on the biochip.

This interaction is highly sensitive and enables an analysis of blood compatibility even in the case of pathology or of weak antigens.

Other types of interaction and other means of detection than those described previously may be used to analyze the blood (detection of viruses, proteins, circulating rare cells, etc.) or other body fluids collected.

The process according to the invention also provides a step of analyzing a sample 810 of given product and a step of comparing the collected body fluid 304 and the sample 810 of given product.

For example, in the case of a blood transfusion, the given product is blood stored in one of the secondary sampling containers 810, separable from the main container 820 of the transfusion bag 800.

Preferably, the analysis means 700 is also capable of analyzing the sample of given product 810 and comparing it with the collected body fluid 304.

The process according to the invention also provides a step of displaying comparison information of the collected body fluid and the sample of given product. For this purpose, the sample collection kit according to the invention comprises a means of displaying comparison information of the collected body fluid and the sample of given product.

In the embodiment illustrated in FIG. 17, the sample collection container 303 is in fluid communication, via a line 306, with a reaction chamber 712.

The line 306 is long enough to enable an operator, when the reaction chamber is ready for the analysis and comparison, to place the chamber 710 on a means (not represented) for attachment to a flow control means 731 similar to that described in FIG. 12. This is equipped with a detection and analysis means 721 and with means 741 for displaying the comparison information $I_C$ (not represented) transmitted by the means 721.

The attachment means may be a clamp sandwiching the reaction chamber 710, so that the position of the chamber is optimal for the detection and analysis via the means 721.

This embodiment avoids disconnecting the chamber from the line 306. The risks of direct contact between the operator and the fluid collected are therefore reduced.

Moreover, the detection and analysis take place on the same perfusion line. Since there is no disconnection between the chamber 710 and the patient (via the sample collection device 200-400, the channel 300, the container 303 and the line 306), it becomes impossible to make a connection error between the chamber and the flow control means 731; there can be no inversion of chamber between one patient and another patient.

In the embodiment illustrated in FIG. 18, the detection means 720 of the analysis means 700, located in the vicinity of the reaction chamber 710, transmits comparison information $I_C$ to a flow control means 730 of a second perfusion (here a blood transfusion circuit). The flow control means 730 is preferably equipped with a means 740 for displaying the comparison information.

Practically, the analysis means 700 is, in this embodiment, located below the catheter of the patient, in the vicinity of the sample collection container 303.

Such an embodiment has the advantage of requiring only a short length of fluid lines (channel 300 and line 305). However, the overall space requirement of the system may be large since it comprises an analysis means 700 and an independent flow control means 730.

In the embodiment illustrated in FIG. 19, the reaction chamber 710 is, as in FIG. 18, connected to the container 303 of collected fluid and to a sample 810 of given product.

When the reaction chamber is ready for the analysis and the comparison, the operator clamps the line 305 (a closure toothed wheel, not represented, is preferably provided for this purpose) and connects the reaction chamber 710 to an analysis means and a flow control means 731. The latter is equipped with a detection and analysis means 721 and a means 741 for displaying the comparison information $I_C$ (not represented) transmitted by the means 721. The connection of the chamber 710 to the control means 731 may be made using an attachment means (not represented).

The attachment means may be a clamp sandwiching the reaction chamber 710, so that the position of the chamber is optimal for the detection and analysis by the means 721.

This embodiment has the advantage of being more compact than that illustrated in FIG. 18. However, it requires a step of fluid disconnection of the reaction chamber 710, which may constitute a risk of contact between the operator and the fluid collected.

In the three preceding embodiments, when the analysis is carried out by the analysis means 700-720-721, the latter transmits to the flow control means 730-731 of the second perfusion, the comparison information $I_C$ of the collected body fluid and the sample of given product.

This information is then displayed owing to display means 740-741.

The nursing staff then know if the product of the second perfusion is compatible with the patient and/or the medical situation which has been diagnosed. In the example of blood transfusion, the nursing staff know if the blood of the transfusion bag is of an ABO group compatible with the ABO group of the patient.

In another example, the nursing staff could determine that the antibiotic present in the perfusion bag does not cause an allergic reaction with the patient.

When the comparison information indicates that the product of the second transfusion is compatible with the patient, the nursing staff may place the second perfusion of product in fluid communication with the fluid circuit of the first perfusion.

This placing in fluid communication is advantageously carried out through flow control means.

This embodiment makes it possible to only connect the bag of product of the second perfusion if it is compatible with the patient. This avoids wasting a bag of product since this system makes it possible to recover the bag considered to be incompatible.

However, it can also be envisaged to make provision for the bag of the second perfusion to already be connected to the control means when the analysis and comparison are carried out.

Next, the nursing staff manually activate a means 900 of flow generation of said product.

According to one preferred embodiment, the process according to the invention comprises a step of blocking the flow of the product of the second perfusion if the comparison information indicates that the body fluid and the product of the second perfusion are incompatible and of permitting the flow of the product of the second perfusion if the comparison information indicates that the body fluid and the product of the second perfusion are compatible.

In this way, if the nursing staff accidentally take the decision to manually generate the flow by activating the generation means 900, the product of the second perfusion does not flow.

For this purpose, the flow control means comprises a solenoid valve in fluid communication with the circuit of the second perfusion.

It can also be envisaged, for certain applications, for the analysis means to also be able to control the flow control means so that it automatically generates flow of the product of the second perfusion if the body fluid and the product of the second perfusion are compatible, and so that it does not generate flow of the product of the second perfusion if the body fluid and the product of the second perfusion are incompatible.

According to another embodiment that is not illustrated, the sample collection device comprises a container, advantageously equipped with a closeable air inlet, connected to tubing that can be connected at its distal end via a connection of Luer lock type. This system may be put in place on a three-way stopcock that is already in place, positioned on an extension or on a stopcock ramp connected on the one hand to the catheter in place on the patient and on the other hand to the perfusion tubing. The sample collection is then carried out by lowering the container, as described previously. This embodiment has the advantage of being very simple. Nevertheless, it leads to a diluted volume (blood and perfusion fluid) and to a filling time that are greater than with the embodiments described previously.

The invention therefore allows a final check on the same perfusion line connected to the patient. Therefore, there are no longer risks between the analysis for the final check and the actual implementation of the treatment itself since the check and the treatment authorization are linked directly to the patient, without potentionally erroneous intervention of the nursing staff.

The object of the process according to the invention is not to diagnose the medical situation (illness, accident, hemorrhage, etc.) and/or to choose the treatment ad hoc since these steps have previously been carried out by the doctor, depending on the medical situation and the patient.

The process aims to ensure that the treatment which will be given is indeed in accordance with the choice of the doctor. For example, the doctor has diagnosed the medical situation X and he/she has chosen to treat the patient Y with the product Z which is compatible with the medical situation X and the patient Y. After this diagnosis, the process according to the invention makes it possible to carry out a final check during the implementation of the treatment, by verifying that it is indeed the product Z, compatible with the medical situation X and the patient Y, which is applied.

For the example of blood, the process according to the invention makes it possible to carry out a final check during the implementation of the transfusion, by verifying that the blood of the transfusion bag, needed for the treatment of the medical situation X previously diagnosed, is compatible with the ABO blood group of patient Y.

This process does not therefore aim to diagnose a medical situation requiring a blood transfusion or to prevent a medical situation requiring a blood transfusion.

It is a method that aims to avoid a medical accident (incompatibility between the treatment product and the patient) and not one that aims to treat a pathological condition.

The invention claimed is:

1. A sample collection device for collecting a sample of a body fluid configured to be incorporated into a fluid circuit of a perfusion of a patient, the fluid circuit of a perfusion comprising a container, a filter, an expansion vessel, a toothed wheel, a perfusion tubing and a perfusion catheter, the arm of a patient being equipped with the perfusion catheter, said sample collection device comprising:
- a sample collection channel comprising a distal end;
- a tubular structure for connection to a distal end of the perfusion tubing, and to a proximal end of the perfusion catheter, the tubular structure comprising a graduation;
- the tubular structure being equipped with a zone ($Z_i$) of intubation of the sample collection channel;
- the zone ($Z_i$) of intubation, including a holding means having a shape of a ring and a membrane embedded inside the ring for the leaktight insertion of the sample collection channel through the membrane in the tubular structure
- a portion of the sample collection channel comprising the distal end, when positioned in the holding means, is pointed toward the perfusion catheter in the flow direction of the perfusion product, from the container of perfusion product to the perfusion catheter, wherein the distal end of the sample collection channel is arranged at a given butt-joining distance ($d_{c1}$) from the proximal end of the perfusion catheter of between 0 cm and 3 cm using the graduation when positioned in the holding means;
- wherein the sample collection device is configured to enable flow of the body fluid into the sample collection channel countercurrent relative to the perfusion product, and wherein the sample collection channel includes a non-return means located at a proximal end of the sample collection channel.

2. The sample collection device as claimed in claim 1, wherein the portion comprising the distal end of the sample collection channel is fixed in the tubular structure, and a portion comprising a proximal end of the sample collection channel emerges outside of the tubular structure level with the intubation zone ($Z_i$).

3. The sample collection device as claimed in claim 1, wherein the membrane is made of a leaktight material configured for retaining its leaktightness after having been pierced.

4. The sample collection device as claimed in claim 3, wherein the leaktight material that retains its leaktightness after having been pierced is chosen from a silicone polymer selected from the group consisting of polydimethylsiloxane (PDMS), polymethyl methacrylate (PMMA), and polyvinyl chloride (PVC).

5. The sample device as claimed in claim 1, wherein the intubation zone comprises a leaktight connector configured for enabling the connection of the tubular structure of the portion of the sample collection channel comprising the distal end.

6. A set comprising for collecting a sample of a body fluid configured to be incorporated into a fluid circuit of a perfusion of a patient, wherein the fluid circuit includes a container, a filter, an expansion vessel, a toothed wheel, a perfusion tubing and a perfusion catheter, the set comprising:
- a sample collection channel having a distal end and a proximal end; and
- a sample collection device comprising:
  - a tubular structure for connection to a distal end of a perfusion tubing, and to a proximal end of the perfusion catheter, the tubular structure comprising a graduation;
- the tubular structure being equipped with a zone ($Z_i$) of intubation of the sample collection channel;
- the zone ($Z_i$) of intubation of the sample collection channel, the zone of intubation including an annular shaped holding member having a leaktight material embedded in said holding member, said holding member configured for the leaktight insertion of the sample collection channel through the leaktight material;
- wherein distal end of the collection channel, when positioned in the holding means, is pointed towards the perfusion catheter in the flow direction of the perfusion product, from the container of perfusion product to the perfusion catheter, wherein the distal end of the sample collection channel is arranged at a given butt-joining distance ($d_{ci}$) from the proximal end of the perfusion catheter of between 0 cm and 3 cm as indicated by the graduation when positioned in the holding means; and
- wherein the sample collection device is configured to enable flow of the body fluid into the sample collection channel countercurrent relative to the perfusion product, and wherein the sample collection channel includes a non-return means located at a proximal end of the sample collection channel.

* * * * *